United States Patent
Wang et al.

(10) Patent No.: US 10,421,938 B2
(45) Date of Patent: Sep. 24, 2019

(54) PLASMA INDUCED MUTATION BREEDING DEVICE

(71) Applicant: Luoyang TMAXTREE Biotechnology Co., Ltd, Luoyang (CN)

(72) Inventors: Liyan Wang, Luoyang (CN); Xianrong Bi, Luoyang (CN)

(73) Assignee: Luoyang TMAXTREE Biotechnology Co., Ltd, Luoyang (CN)

( * ) Notice: Subject to any disclaimer, the term of this patent is extended or adjusted under 35 U.S.C. 154(b) by 253 days.

(21) Appl. No.: 15/447,937

(22) Filed: Mar. 2, 2017

(65) Prior Publication Data

US 2017/0267963 A1 Sep. 21, 2017

(30) Foreign Application Priority Data

Mar. 16, 2016 (CN) .......................... 2016 1 0152250

(51) Int. Cl.
*C12M 1/42* (2006.01)
*C12M 1/36* (2006.01)
(Continued)

(52) U.S. Cl.
CPC ............ *C12M 35/02* (2013.01); *C12M 23/34* (2013.01); *C12M 23/48* (2013.01); *C12M 23/50* (2013.01);
(Continued)

(58) Field of Classification Search
CPC . C12M 35/08; C12N 15/8206; C12N 15/8207
See application file for complete search history.

(56) References Cited

U.S. PATENT DOCUMENTS

2004/0110297 A1* 6/2004 Miyoshi ................. C12M 35/02
435/459

FOREIGN PATENT DOCUMENTS

CN 102382763 A1 3/2012
CN 202297604 A1 7/2012
(Continued)

OTHER PUBLICATIONS

English language machine translation of CN204874543, pp. 1-5, accessed Jan. 6, 2019. (Year: 2019).*
(Continued)

*Primary Examiner* — William H. Beisner
(74) *Attorney, Agent, or Firm* — Adam Warwick Bell; Matthew Rupert Kaser

(57) ABSTRACT

The invention relates to a novel plasma induced mutation breeding device which comprises: a sample treatment system including a sterile working compartment free of bioactive contaminant; a plasma generator; a radio frequency (RF) power module connected with the plasma generator; a cooling system for cooling the plasma generator; a detection system including a gas flow controller for controlling the gas flow which generates the plasma jet and a temperature sensor for detecting the temperature of the jet emitted by the plasma generator; and a control system with an operation panel and a controller for controlling the operation of the mutation breeding device, wherein the controller is connected with the RF power module, gas flow controller, temperature sensor, cooling system as well as the operation panel, respectively, and said plasma generator stably emits the plasma jet at 37±3° C. during the biological sample processing.

8 Claims, 4 Drawing Sheets

(51) Int. Cl.
   C12M 1/34    (2006.01)
   C12M 1/00    (2006.01)
   C12M 3/00    (2006.01)
   C12M 1/12    (2006.01)
   C12M 1/02    (2006.01)

(52) U.S. Cl.
   CPC ............ C12M 29/06 (2013.01); C12M 35/08
           (2013.01); C12M 37/00 (2013.01); C12M
           41/12 (2013.01); C12M 41/18 (2013.01);
           C12M 41/34 (2013.01); C12M 41/48
                                      (2013.01)

(56) References Cited

FOREIGN PATENT DOCUMENTS

| | | | |
|---|---|---|---|
| CN | 203700376 | A1 | 7/2014 |
| CN | 103981091 | A1 | 8/2014 |
| CN | 203960219 | A1 | 11/2014 |
| CN | 204874543 | U * | 12/2015 |
| JP | 2002-352998 | A1 | 12/2002 |
| JP | 2005-113202 | A1 | 4/2005 |
| JP | 2007-037422 | A1 | 2/2007 |
| JP | 2009-032717 | A1 | 2/2009 |
| JP | 2014-173150 | A1 | 9/2014 |

OTHER PUBLICATIONS

He-Ping Li, Zhi-Bin Wang, Nan Ge, Pei-Si Le, Hao Wu, Yuan Lu, Li-Yan Wang, Chong Zhang, Cheng-Yu Bao, Xin-Hui Xing: "Studies on the Physical Characteristics of the Radio-Frequency Atmospheric-Pressure Glow Discharge Plasmas for the Genome Mutation of Methylosinus Trichosporium"; IEEE Transactions on Plasma Science, vol. 40, No. 11 Nov. 2012, pp. 1-9.

Liang Wang, Xusheng Chen, Guangyao Wu, Shuang Li, Xin Zeng, Xidong Ren, Lei Tang, Zhonggui Mai: "Improved ε-poly-L-lysine production of Streptomyces sp. FEEL-1 by atmospheric and room temperature plasma mutagenesis and streptomycin resistence screening"; Ann Microbiol (2015) 65:2009-2017, DOI 10.1007/s13213-015-1039-8, Published Feb. 3, 2015, pp. 1-10.

Xue Zhang, Chong Zhang, Qian-Qian Zhou, Xiao-Fei Zhang, Li-Yan Wang, Hai-Bo Chang, He-Ping Li, Yoshimitsu Oda, Xin-Hui Xing: "Quantitative evaluation of DNA damage and mutation rate by atmospheric and room-temperature plasma (ARTP) and conventional mutagenesis"; Appl Microbiol Biotechnol (2015) 99:5639-5646, DOI 10.1007/s00253-015-6678-y, pp. 1-9.

L.-Y. Wang, Z.-L. Huange, G. Li, H.-X. Zhao, X.-H. Xing, W.-T. Sun, H.-P. Li, Z.-X. Gou, C.-Y. Bao: "Novel mutation breeding methog for Streptomyces avermitilis using and atmospheric pressure glow discharge plasma"; Journal of Applied Microbiology, 108 (2010) 851-858, pp. 1-9.

* cited by examiner

PLASMA INDUCED MUTATION BREEDING DEVICE

FIELD OF THE INVENTION

The invention belongs to the plasma processing device field, specifically, relates to a novel plasma induced mutation breeding device for biological breeding.

BACKGROUND OF THE INVENTION

Microbial strain with good quality is the center of bio-industry, and how to effectively utilize biological mutagenesis technique to achieve rapid microbial strain optimization is an important task for biological industry. Conventional biological mutagenesis methods normally have disadvantages of low efficiency, heavy workload, and low specificity, etc.; chemical mutagenesis also tends to cause injuries to the operation staff, bring contamination to the environment; and physical mutagenesis has poor mutagenesis capability and the microorganism employed will display resistance after reuse; also, other methods often require professional and complicated devices, and some of them cost very high. Therefore, conventional biological mutagenesis methods are not suitable for the development of industrial bacterial strains, and a new, highly effective mutation breeding technique which can be operated easily, increase the efficiency and shorten the screen cycle of the mutation breeding is in demand.

SUMMARY OF THE INVENTION

Conventional mutation breeding has the disadvantages of long cycle, slow process, and it is also difficult to achieve mutations effectively in strains by conventional mutation breeding. As a new mutation breeding technique, plasma technique does not only overcome above disadvantages but is also more efficient and cost less comparing with the genetic engineering method. Especially for biological cells which have complicated metabolism network, non-transgenic mutagenesis has its unique advantages. Plasma is the forth state of substance existing together with solid, liquid and gas states. It is majorly composed of free electrons and charged particles (charged ions) but appears electrically neutral as a total. It is reported that majority of active particles in plasma can act on different biological samples and bring improvements for various aimed properties and has good application prospect in biotech field.

Current plasma induced mutation breeding device can only process one or a few samples at once. However, processing a large amount of biological samples is normally required in present biological breeding field, and accordingly the plasma generator needs to continue working for a very long time. In this case, the RF (radio frequency) power keeps in working condition to output RF energy for the plasma generator, and the plasma generator continues to generate plasma jet, and the temperature of the plasma jet generated keeps increasing with the increase of the operating time, thereby cause the device unable to stably provide plasma jet within given temperature range for long term. Meanwhile, if the device is used in summer or tropics for a long time, the temperature of the plasma jet will increase even faster, and in this case, it is more difficult to keep the temperature of the jet in stable range for a long term.

As said above, in a device processing multiple samples for long term, RF power need to emit RF to the plasma generator in a stable state. However, in regular mutation breeding devices, the RF power will be affected by interference from other components in the device, causing RF power unable to stably emit RF energy, and therefore the plasma generator cannot emit stable jet. Furthermore, if the mutation breeding device is used for a long term or in hot region or season, the temperature of the plasma generator will increase gradually during operation, and this increased temperature will change the capacitance value of the plasma generator, at this point, if the setting of the RF power is not adjusted in time, the jet will also be unstable. Current existing plasma induced mutation breeding devices normally set up a manual adapter for the RF power to match the latter, and when the RF power is interfered or the capacitance value of the plasma generator is altered, the adaptor connected with the RF power and the plasma generator can be adjusted manually to make the two match each other so that the RF power will transfer appropriate RF to the plasma generator and further emit appropriate plasma jet by the plasma generator. Therefore, when the interference is severe or the temperature change is significant, the operation need to stop frequently or at any time to manually perform the adaptation, therefore, the effects and efficiency of the processing by current breeding devices on the biological samples will be largely affected. In addition, to block the unnecessary internal interference within the plasma device, a conventional mean is to use steel which has better grounding property as the housing to block the internal interference of the device, however, this may result in a very heavy weight and huge size of the entire mutation breeding device.

While processing multiple samples, if the amount is large, samples to be processed have to wait for a long period in the working compartment before treatment, which will dramatically increase the risk of contamination for those samples. Furthermore, if the samples to be treated are liquids, after placing in the sterile working compartment for a long period, liquid portions of the biological samples such as culture medium will evaporate, thereby causing inadequate volume of the sample for treatment when the treatment begins. In another aspect, if the processed samples are not collected in time, result of the mutation breeding will be affected. Therefore, new plasma induced mutation breeding device which adds the samples to be treated immediately before emitting plasma jet to the sterile working compartment and also collects the samples rapidly after the treatment is in demand.

The invention provides a novel plasma induced mutation breeding device to solve the existing problem in the art. The technical solutions of the invention are as below:

(1). A plasma induced mutation breeding device, which comprises:

a sample treatment system including a sterile compartment free of bioactive contaminant, a plasma generator, and radio frequency (RF) power module connected with the plasma generator;

a cooling system for cooling the plasma generator;

a detection system including a gas flow controller for controlling the gas flow which generates the plasma jet and a temperature sensor for detecting the temperature of the jet emitted by the plasma generator; and a control system with an operation panel and a controller for controlling the operation of the mutation breeding device, wherein the controller is connected with the RF power module, gas flow controller, temperature sensor, cooling system as well as the operation panel, respectively, and said plasma generator stably emits a plasma jet at 37±3° C. during the biological sample processing.

(2). The plasma induced mutation breeding device of (1), wherein the RF power module includes a RF power and an adaptor which automatically matches the RF power, and said RF power is connected with the plasma generator via the adaptor.

(3). The plasma induced mutation breeding device of (2), wherein the sample treatment system, detection system and controller are disposed within one housing, the cooling system is disposed outside the housing, the housing is an aluminum profiles housing, and the sterile working compartment has an installation position for a sterilization mean.

(4). The plasma induced mutation breeding device of any one of (1)-(3), wherein the temperature sensor feedback the result of the detected jet temperature to the control system and according to the result, the cooling system maintains the temperature of the plasma jet emitted by the plasma generator at 37±3° C. during the whole sample treatment process.

(5). The plasma induced mutation breeding device of any one of (1)-(4), wherein the plasma generator has a coaxial structure, and the volume of the sample to be treated is not more than 200 μl, preferably not more than 150 μl, further preferably not more than 100 μl, not more than 50 μl, not more than 20 μl, and is not less than 3 μl, preferably not less than 5 μl.

(6). The plasma induced mutation breeding device of any one of (1)-(4), wherein the plasma generator has a flat structure, and the volume of the sample to be treated is 0.1 mL-10 mL, preferably 0.5 mL-10 mL, and further preferably 1 mL-5 mL.

(7). The plasma induced mutation breeding device of any one of (1)-(6), wherein a stepped motor and a loading stage are disposed within the sterile working compartment, and the controller lift or horizontally rotate the loading stage by controlling the stepped motor to automatically treat multiple samples and also control the rotation speed of the loading stage to replace the treated sample with the next one to be treated within a 5 seconds interval.

(8). The plasma induced mutation breeding device of any one of (1)-(6), wherein a carrier conveyor, a sample injector, and a sample recovery belt are disposed within the sterile working compartment.

(9). The plasma induced mutation breeding device of (8), wherein within 5 seconds after being added by the sample injector, the sample is delivered by the carrier conveyor to a position under the nozzle for jetting, and then the treated sample is recovered by the sample recovery belt within 5 seconds.

(10). The plasma induced mutation breeding device of (9), wherein a container accommodating protective agent for recovering the sample is disposed on the sample recovery belt.

The technical effects of the invention are:

According to the plasma induced mutation of the invention, even in hot summer or tropical region, multiple samples can be continuously processed by plasma induced mutation breeding device for a long time, and the temperature of the jet emitted by the plasma generator can be kept at the range of 37±3° C., thereby inducing appropriate emergency repair system in microorganism and then effectively stimulate mutations to achieve mutation breeding for a large amount of samples effectively.

Since the appropriate plasma generator of the mutation breeding device can be replaced according to the sample to be treated, the device can treat samples in different types and sizes. For example, varieties of samples from bacteria, actinomycetes, fungi to plant cells, animal cells, plant tissue, animal tissue etc. can be processed by the device of the invention.

Because the adaptor in the RF power module will match the RF power and plasma generator automatically according to the surrounding environment and temperature change to prevent from affecting by the outside environment and interference from the other components, the device of the invention ensures that the plasma generator will stably emit plasma jet at the temperature in the range of 37±3° C. In addition, because the adaptor and RF power are modularized, compared to existing plasma induced mutation breeding device, the size of the device in this invention is reduced by ⅓. Also, because the lighter material aluminum profiles can be used in this device, the weight can also be reduced by ⅓ compared to the existing device. During the whole operation process, manual matching operation is not necessary, which reduce the working strength for the operation staff.

According to the invention, the plasma induced mutation breeding device can process a large amount of biological samples. And during multiple samples treatment process, the device can achieve immediate sampling, treatment, and collecting after the treatment, so that to avoid the risk of dry and contamination for other samples while the waiting period. The device can collect samples after the processing in time to ensure the effect of the mutation breeding.

Figure 1:
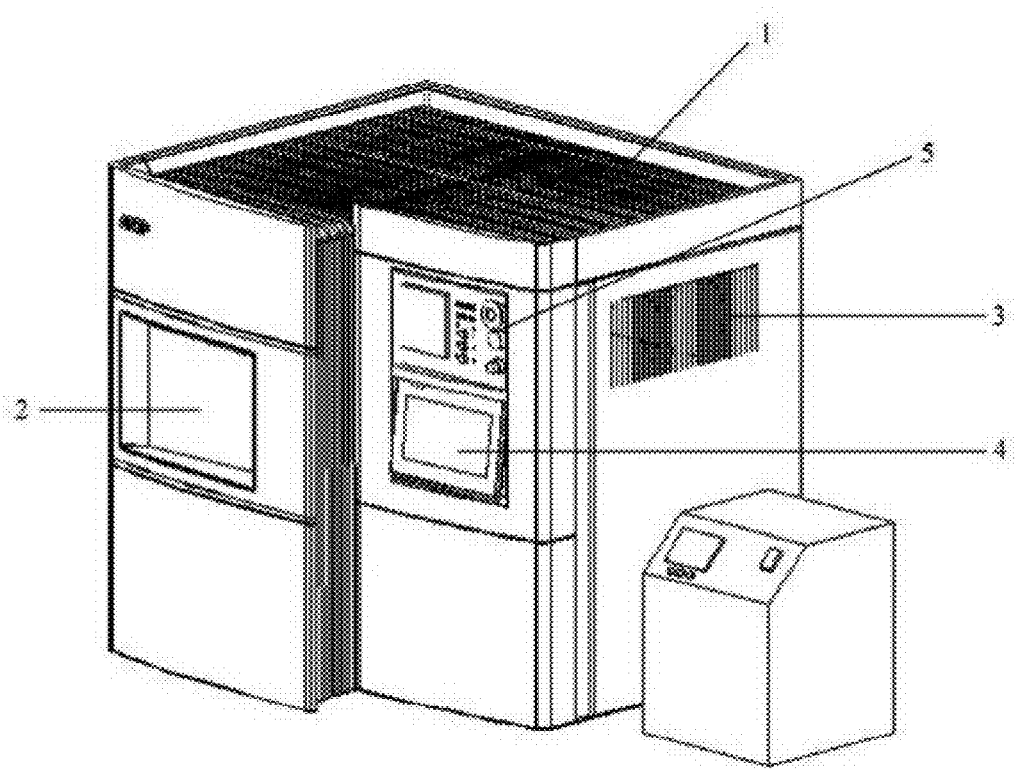
FIG. 1 shows the schematic diagram of the entire structure in an embodiment of the plasma induced mutation breeding device in this invention.

SYMBOL DESCRIPTION 1 housing;
2 sterile working compartment;
3 vent;
4 operation panel;
5 power control button;
6 controller;
7 plasma generator;
8 RF power module;
10 loading stage;
12 nozzle;
13 temperature sensor;
16 gas flow controller;
20 stepped motor;
32 carrier conveyor;
33 sample injector;
34 sample recovery belt.

DETAILED DESCRIPTION OF THE INVENTION

The invention will be further described below together with figures.

The plasma induced mutation breeding device of the invention can be used under a regular pressure and temperature condition to induce mutation breeding in biological samples through plasma technique. It comprises sample treatment system, cooling system, detection system and control system. Said sample treatment system includes sterile working compartment 2 free of bioactive contaminant, plasma generator 7, and RF power module 8 connected with plasma generator 7; the cooling system acts on plasma generator 7 to cool down the plasma generator; the detection system includes gas flow controller 16 which controls the flow of the gas producing plasma jet and temperature sensor 13 which detects temperature of the jet emitted by the plasma generator; the control system includes operation panel 4 and controller 6, and is used to control the operation of the mutation breeding device, wherein controller 6 is connected with RF power module 8, gas flow controller 16, temperature sensor 13, cooling system and control panel 4, respectively. Plasma generator 7 of the plasma induced mutation breeding device of the invention stably emits jet at 37±3° C. while treating all of the samples. Because the plasma induced mutation breeding device of the invention can keep the emitted plasma jet for treating the biological samples at 37±3° C., it can induce appropriate emergency repair system in microorganism, and thereby effectively perform breeding on the biological samples to be treated.

In one embodiment of the invention, RF power module 8 includes RF power 8' and adaptor 8" which automatically matches with RF power. The RF power 8' is connected with plasma generator 7 through adaptor 8", so that the RF power 8' can transfer RF source to adaptor 8", and then to plasma generator 7 after being matched by adaptor 8", thus gas such as helium is converted to energy in plasma state (i.e. plasma jet). There is a signal line between RF power 8' and adaptor 8", which sends and collects feedback signal. There is also a RF line connecting adaptor 8" and plasma generator 7, which collects information of the physical property of plasma generator 7 (such as capacitance value), and adaptor 8" can feedback information of the physical property to RF power 8' through the signal line. When the temperature of plasma generator 7 changes significantly with the environment or the temperature of plasma generator 7 itself due to the long term operation, the physical property of plasma generator 7 (such as capacitance value) will change, and the adaptor 8" will detect this change and match its value automatically, and then feedback the signal to RF power 8', thereby RF power 8' will adjust the RF it emits according to the feedback signal. In this embodiment, matching the temperature change of the plasma generator and the external environment automatically will enable the plasma generator stably receive the RF source from the RF power and the emit plasma jet at the range of 37±3° C. Furthermore, modularization of the RF power 8' and adaptor 8" will dramatically decrease the size of the RF power module 8 which is ⅓ less compared to the RF power module in existing plasma induced mutation breeding module.

Figure 5:
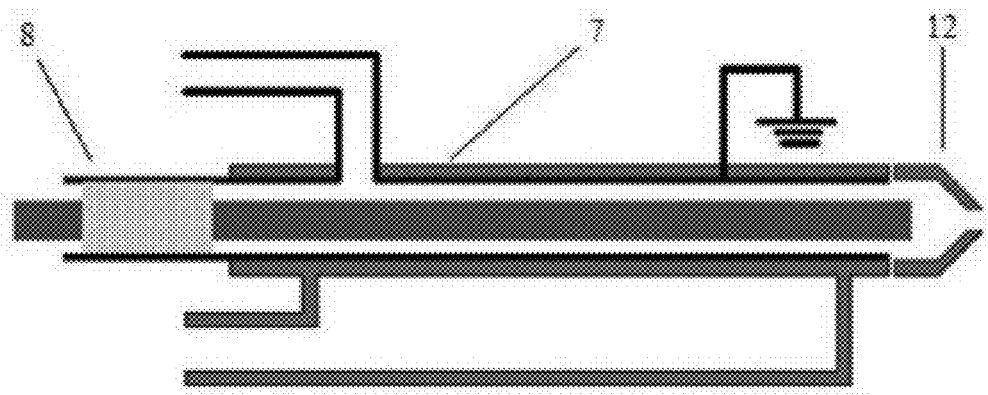
FIG. 5 shows the plasma generator with coaxial structure in an embodiment of the plasma induced mutation breeding device in this invention.

In one embodiment of the plasma induced mutation breeding device, plasma generator 7 has a coaxial structure (as below, referred as coaxial electrode occasionally), and the plasma generator with a coaxial structure employs coaxial naked metal to produce the plasma jet. One example of the coaxial electrode is shown in FIG. 5. The outlet of the coaxial electrode forms nozzle 12, and the sectional area of nozzle 12 is a circle with a diameter between 8 and 20 mm Although the nozzle of the coaxial electrode for plasma jet has a small sectional area, it can achieve centralized and stabilized jet, therefore, the plasma jet produced by the coaxial electrode is suitable for procession samples with small area and volume, such as culture suspension of bacteria, actinomycetes, fungi or suspension of spore. When producing plasma jet by the coaxial electrode, the volume of the sample to be processed is normally not more than 200 μl, preferably not more than 150 μl, further preferably not more than 100 μl, not more than 50 μl, not more than 20 μl, and is not less than 3 μl, and preferably not less than 5 μl.

Figure 6:
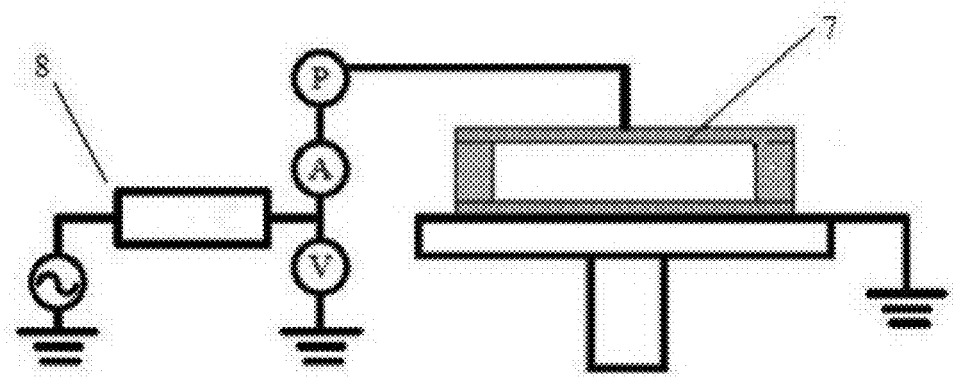
FIG. 6 shows the plasma generator with flat structure in an embodiment of the plasma induced mutation breeding device in this invention.

In another embodiment of the plasma induced mutation breeding device of the present application, plasma generator 7 has a flat structure (as below, referred as flat electrode occasionally). For example, a specific example of the plasma generator with a flat structure is shown in CN Publication No. CN100405879C and wherein the flat plasma generator can be used for processing samples with larger size, such as seed, seedling and callus of plant. When producing the plasma jet with flat electrode, the volume of the sample to be processed is normally between 0.1 mL and 10 mL, preferably between 0.5 mL and 10 mL, and further preferably between 1 mL and 5 mL. One example of the plasma generator with flat structure is shown in FIG. 6.

FIG. 1 shows the entire structure in an embodiment of the plasma induced mutation breeding device of the invention. In this example, the sample treatment system, detection system and control system are disposed within housing 1, and the cooling system is disposed outside housing 1, such as the small box structure set next to housing 1.

In another embodiment of the plasma induced mutation breeding device of the present application, the material of the housing is aluminum profiles. The total weight of the entire device can be reduced significantly by aluminum profiles, and compared to the existing devices, and the weight can be reduced by ⅓. In prior art, aluminum profiles is normally considered to have poor grounding property, which makes it not able to block the interference between the components within the housing. For this reason, steel material which has better grounding property is normally used in existing devices. However, because the plasma induced mutation breeding device of the present invention utilizes above said RF power module 8, the interference is largely reduced, thereby aluminum profiles material can be used for the housing for less weight and better appearance.

In one embodiment of the invention, the cooling system is air cooling system including external disposed water pump, water tank and radiator which are sequentially connected, wherein two ends of plasma generator 7 are connected with water pump and radiator respectively to form circulation.

In another embodiment of the present application, the cooling system is water cooling system including external disposed cooling water circulator connected with plasma generator 7. In this case, the external disposed cooling water circulator is connected with housing 1 by the way as below: housing 1 has an inlet and an outlet for water, i.e., two ports, and the water outlet of the external disposed cooling water circulator is connected to the water inlet of housing 1 so that water will flow into housing 1 and then to the water inlet of plasma generator 7, the water outlet of plasma generator 7 is connected with the water outlet of housing 1, and finally to water inlet of cooling machine to form the circulation.

In the embodiments of the invention, the water cooling system is preferred as the cooling system.

In one embodiment of the invention, temperature sensor 13 feeds back the detected jet temperature result to the control system, and control the operation of the cooling system according to the result so as to keep the plasma jet emitted from plasma generator 7 at 37±3° C. during the entire sample treatment process. By this way, it ensures that plasma generator 7 can stably emit plasma jet at temperature in the range of 37±3° C., so that the device of the invention can be stably used for a long time during hot season and in tropical region.

In one embodiment of the invention, temperature sensor 13 will feed back the detected jet temperature result to the control system, if the temperature is below the range of 37±3° C., controller 6 will send a "preheating" signal according to the feedback result sent by the temperature sensor 13, which will further be shown on the operation panel to remind the operation staff stop adding samples. When RF power module 8 keeps sending RF, the temperature of the plasma jet emitted by plasma generator 7 will gradually increase, if the temperature increases to 37±3° C., temperature sensor 13 will feedback the detected jet temperature to the control system, in this case, a "ready to treatment" signal will be shown on the operation panel to remind the operation staff continue adding samples.

In one embodiment of the invention, the sterile working compartment 2 has an installation position for a sterilization mean, wherein the position can be a preset UV lamp holder with a through-hole for power cable in the sterile working compartment, and said sterilization mean can be a UV lamp connected with the controller. In another embodiment, the position for the sterilization mean is a through-hole opened on the wall of the sterile working compartment, and the sterile mean can be a supply tube for chemical sterilizing gas, wherein the supply tube is connected with an external chemical sterilizing gas tank and also inserts into said sterile working compartment via the through-hole.

Figure 2:
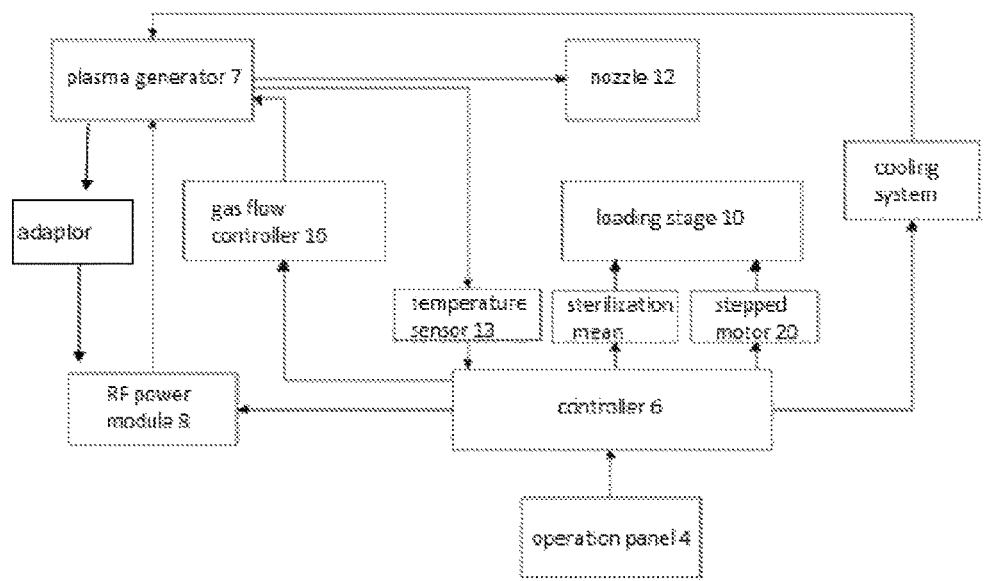
FIG. 2 shows the schematic diagram of the internal structure in an embodiment of the plasma induced mutation breeding device in this invention.

In one embodiment of the invention, stepped motor 20 and a loading stage 10 are disposed within sterile working compartment 2, and controller 6 lifts or horizontally rotates loading stage 10 by controlling stepped motor 20 to treat multiple samples automatically, the controller 6 also controls the rotation speed of the loading stage to replace the treated sample with the next one to be treated within 5 s interval. FIG. 2 shows the schematic diagram of the internal structure in one embodiment of the plasma induced mutation breeding device of the invention.

When controller 6 rotates loading stage 10 horizontally by stepped motor 20, multiple recesses for keeping sample are set circumferentially on loading stage 10, and by horizontally rotating loading stage 10, the recesses will sequentially direct to the nozzle. Samples to be treated, especially the ones with small volume, are disposed in each recesses, and then operation panel 4 controls stepped motor 20 through controller 6 to horizontally rotate loading stage 10, so that the recesses with samples to be treated will sequentially direct to nozzle 12 of the coaxial electrode or the flat electrode and plasma generator 7 will start to produce plasma jet to treat the samples. After finishing the treatment, loading stage 10 will horizontally rotate for certain angle again to let the next recess with samples to be treated rotate to the position directing to nozzle 12 of the coaxial electrode or the flat electrode to continue the treatment. Hence, large quantities of samples, especially the ones with small volume will be processed automatically and continuously for mutagenesis through the device of the invention with simple structure.

The device of the invention has an outstanding application value in the biological filed because it ensures that the biological material will be treated by plasma effectively and rapidly without contamination by other impurities, microbes and the like. By disposing a stepped motor and loading stage in the sterile working compartment, the operation panel of the control system controls the stepped motor through the controller to lift or horizontally rotate the loading stage so as to automatically treat multiple samples. This stepped motor control technique cooperates with the structure of the loading stage to enable samples to be treated lift or horizontally rotate together with the loading stage. After one sample is finished, it will be replaced by the next one automatically, so that a large amount of samples will be processed automatically and continuously, which avoids manually loading and removing samples by the operation staff and ensure the whole process will not be contaminated. This approach reduces labor cost and also increases efficiency of the mutation breeding. This control panel achieves multiple functions including automatic sterilization, automatic monitoring and controlling, which can effectively finish the plasma induced mutation breeding under room temperature and atmospheric pressure. Furthermore, the rotation speed of the loading stage can be controlled so as to replace with the next sample to be treated within a 5 s interval after the current treatment.

In one embodiment of the invention, a temperature display, a gas flow setting button, a gas flow monitor, a treatment time setting button, a sterilization mean control button, a stepped motor control button and a light button are disposed on the operation panel, wherein the controller can be a programmable logic controller, and this controller can be connected with the operation panel through serial cable or field bus.

Figure 3:
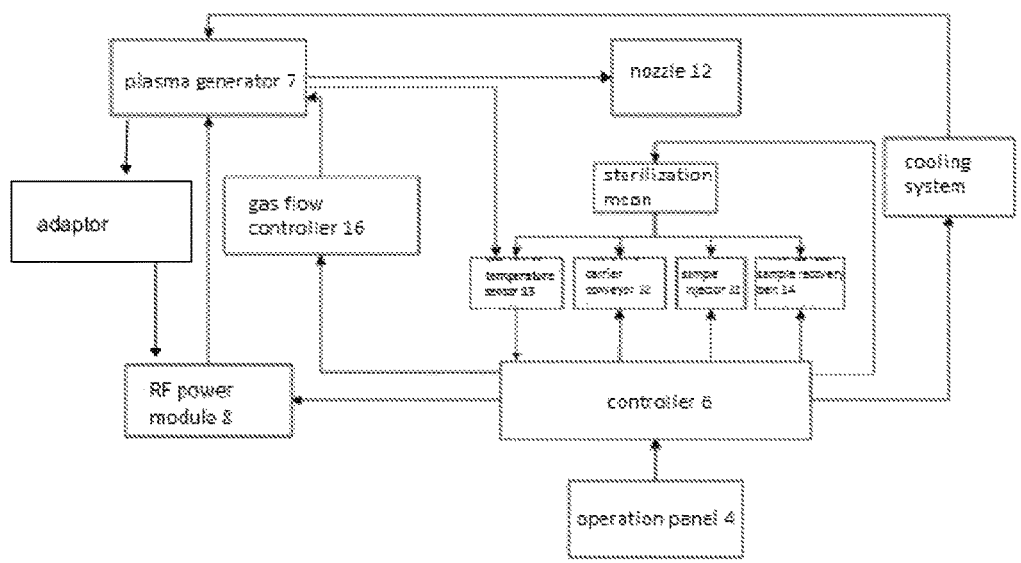
FIG. 3 shows the schematic diagram of the internal structure in another embodiment of the plasma induced mutation breeding device in this invention.
Figure 4:
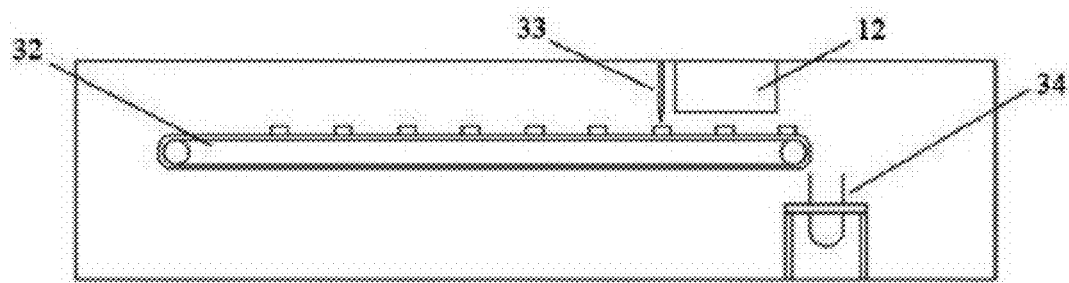
FIG. 4 shows the schematic diagram of the sampling system in an embodiment of the plasma induced mutation breeding device in this invention.

In one embodiment of the invention, a carrier conveyor 32, a sample injector 33, and a sample recovery belt 34 are disposed within the sterile compartment 2. FIG. 3 shows a schematic diagram of the internal structure in one embodiment of the plasma induced mutation breeding device of the invention. FIG. 4 shows a general structure of the sampling system.

Said carrier conveyor 32 and sample recovery belt 34 use tracks for delivery, wherein multiple hole-sites for holding multiple slides are disposed on the track from right to left, and sample injector 33 for filling samples can be set at one end of conveyor belt 32, and nozzle 12 of the coaxial electrode or the flat electrode of plasma generator 7 can be set at one side of sample injector 33. While running, the hole-sites on the carrier conveyor closest to sample injector 33 is transferred to the direct below of sample injector 33 for adding sample, then the hole-site will be moved to the direct below of nozzle 12 for treatment, and after treatment it will be moved to the edge of carrier conveyor 32 and further fall into a container (such as EP tube) filled with protective agent, and subsequently the container with the sample will move automatically with sample recovery belt 34, meanwhile the next empty container will take the original place. The next numbered sample will be treated in a similar way.

In this embodiment, the protective agent can be, for example, liquid culture medium for culturing biological samples or osmotic stabilizer such as sterile physiological saline with concentration about 0.8%.

By using above sampling system, within 5 s after adding sample by sample injector 33, the sample will be delivered to the directly below of nozzle 12 by carrier conveyor 32 for jet treatment, and after treatment, the sample is recovered by sample recovery belt 34 within 5 s. According the invention, large quantities of samples can be treated by the plasma induced mutation breeding device of the invention. During the treatment, sampling can be performed immediately before the treatment, and the processed samples can be collected immediately after the treatment, which prevents the samples from risks such as drying and contamination during the waiting period and the immediate collecting after the treatment ensures the result of the mutation breeding.

In one embodiment of the invention, a temperature display, a gas flow setting button, a gas flow monitor, a treatment time setting button, a sterilization mean control button, a carrier conveyor control button, a sample injector control button, a sample recovery belt control button and a light button can be disposed on the operation panel, wherein the controller can be a programmable logic controller, and this controller can be connected with the operation panel through serial cable or field bus.

The detection system of the invention includes gas flow controller 16 and temperature sensor 13. Gas flow controller 16 is connected with plasma generator 7, and the temperature 13 is positioned close to nozzle 12 of the coaxial electrode or the flat electrode of plasma generator 7, so as to detect the temperature of the jet emitted by nozzle 12 of the coaxial electrode or the flat electrode. Hose temperature probe can be used for temperature sensor 13 to adjust its angle position, displaying the temperature of sterile working compartment 2 and the jet emitted from nozzle 12 of the coaxial electrode or flat electrode of plasma generator 7

The control system includes operation panel 4, power control button 5 and controller 6. In one embodiment, controller 6 is connected with stepped motor 20, RF power module 8, gas flow controller 16, sterilization mean, lighting system, temperature sensor 13, cooling system and operation panel 4, respectively. Controller 6 preferably is a programmable logic controller, and this controller can be connected with operation panel 4 through serial cable or field bus.

In another embodiment, controller 6 is connected with carrier conveyor 32, sample injector 33, sample recovery belt 34, RF power module 8, gas flow controller 16, sterilization mean, lighting system, temperature sensor 13, cooling system and operation panel 4, respectively. Controller 6 preferably is a programmable logic controller, and this controller can be connected with the operation panel 4 through serial cable or field bus.

Operation panel 4 is disposed outside housing 1, i.e. panel 4 is disposed on the outside wall of housing 1 for the operation staff to operate controller 6. A temperature display, a gas flow setting button, a gas flow monitor, a treatment time setting button, a light button, a parameter setting display button and a device description button, as well as a sterilization mean control button, a stepped motor control button and/or a carrier conveyor, sample injector and sample recovery belt button and the like can also be disposed on operation panel 4. Operation panel 4 preferably is a LCD touch screen, i.e. a LCD touch screen with "current date and time" display screen, "gas flow display and setting" screen, "temperature display" screen, "treatment time" screen, "light" screen, "sterilization mean" screen and the like. By gas flow display and setting screen, supplied gas flow can be monitored and controlled in real time. When gas flow need to be set, the operation staff can click the gas flow setting button on panel 4, and a "number setting interface" window will pop up from the system, after input numbers, click enter button to confirm the input value. Then controller 6 will adjust the gas flow to the new set value which will be shown on the gas flow display. A gas flow value beyond the given range cannot be set, and in this case, the displayed number will keep being 0. "Temperature display" screen is to display probe detected temperature value which mostly indicates the ambient temperature of the working plasma generator.

The operation panel of the invention can set the gas flow, treatment time and control the light and sterilization mean, as well as the stepped motor, carrier conveyor, sample injector and sample recovery belt, so that the device can achieve continuous and automatic processing, monitoring and controlling function. The user friendly interface of the device has comprehensive functions and is easy to operate. It can excite the gas to generate plasma for mutagenesis processing biological samples, which has good application prospect in biotech field.

EXAMPLES

The plasma induced mutation breeding device of the invention will further be illustrated by the following examples.

Example 1

DNA Damage Degree of the Samples After Treated by Plasma Jet at Different Temperature DNA damage is the most direct reason for mutagenesis. During the damage, SOS response will occur in bacteria by the co-function of lexA and recA, and the induced SOS level can be detected by β-galactosidase activity, which indicates the level of DNA damage. DNA damage is characterized by Umu-test method (umu-test AT kit (Isesaki, Japan)), wherein 2-nitrophenyl-β-D-galactopyranoside is used as the substrate, and the activity of β-galactosidase is measured by spectrophotometry to characterize the extent of the induced SOS and to further illustrate the DNA damage degree.

1. Bacteria Strain: *S. typhimurium* NM2009 from the umu-test AT kit of Isesaki, Japan.

2. Reagent: SDS (sodium dodecyl sulfate), DTT (dithiothreitol), ONPG (o-nitrophenyl β-D-galactopyranoside), HEPES (4-hydroxyethyl piperazine acetic acid), ampicillin, chloramphenicol, NTG (nitrosoguanidine), citric acid, sodium citrate, monopotassium phosphate, tryptone, $Na_2CO_3$, disodium hydrogen phosphate, sodium dihydrogen phosphate, which are all commercial available.

3. Medium Culture and Reagent:

TGA culture medium: dissolve 10 g tryptone, 5 g NaCl, 11.9 g HEPES into 900 mL water, adjust pH to 7.0±0.2, and dilute to 970 mL, then autoclave. Dissolve 2 g D(+) glucose into 30 mL water, autoclave.

LB culture medium: tryptone 1%, yeast extract 0.5%, NaCl 1%, agar 2%, distilled water.

B buffer: dissolve 40.6 g $Na_2HPO_4.12H_2O$ 6.2 g $NaH_2PO_4.2H_2O$, 0.75 g KCl, 0.25 g $MgSO_4.7H_2O$ into 900 mL water. Adjust pH to 7.0±0.2, add 1.0 g SDS, and dilute to 1000 ml, then add 0.154 gDTT, seal and store at 4° C.

Phosphate buffer (P-Buffer): dissolve 2.18 g $Na_2HPO_4$. $12H_2O$, 0.61 g $NaH_2PO_4.2H_2O$ into 100 mL water, adjust pH to 7.0±0.2, autoclave (121° C., 20 min), seal and store at 4° C.

ONPG buffer: dissolve 18 mg ONPG into 4 mL phosphate buffer, shake in dark for 2 h till dissolved (or wrap in foil).

Reaction termination buffer: dissolve 106 g $Na_2CO_3$ into 900 mL water and dilute to 1000 mL, store at room temperature.

Equipment: sterile 96 well plate, microplate reader, 20 16 mm glass dishes, 1.5 ml EP tube, pipettor.

4. Experimental Procedure (1) Activation and Pre-Culture of the Strain

S. typhimurium NM2009 is plate-activated by LB solid culture medium supplemented with Ampicillin sodium (25 μg·ml$^{-1}$) and Chloromycetin (25 μg·ml$^{-1}$). The activated strain is transferred to TGA liquid culture medium and pre-cultured overnight. Transfer to TGA culture medium at a ratio of 10%, pre-culture at 37° C. till the bacteria grow to log-phase.

(2) Mutagenesis of the Bacteria

Plasma mutagenesis: add 100 μL pre-cultured bacteria to each 16 mm diameter glass dish, 6 experiments in total and every one experiment are repeated 3 times. Mutagenesis condition: gas flow 10 slpm, power 120 w, the distance between nozzle 12 of the plasma generator and the sample is 2 mm, measure the temperature of the plasma jet, and keep the temperature of the plasma jet at 28° C., 34° C., 37° C., 40° C., 45° C. to induce mutation for 60 s. After irradiation, bacteria solution less than 100 μL will be complemented to 100 μL by TGA culture medium.

(3) Post-Treatment Culture

Take 30 μL bacteria solution from above 100 μL post-treatment sample, and add the bacteria solution to 96 well plate, meanwhile add 270 μL GTA culture medium. Culture medium without bacteria solution and plasma treatment is used as blank control, and culture medium with bacteria solution but without plasma treatment is used as negative control. Culture at 37° C., 100 r·min$^{-1}$ for 2 h. Then measure $A_{600}$.

(4) β-Galactosidase Activity Test

Transfer 30 μL post-treatment bacteria solution to a new 96 well plate. Meanwhile add 120 μL B buffer, 30 μL ONPG substrate solution. React at 28° C. for 30 min Add 120 μL above reaction termination solution. Measure $A_{420}$ to characterize activity of β-galactosidase.

(5) Result and Calculation

For different genetic toxicity experiments, growth factor G and induction ratio Ir are calculated by using following mum/sos/test assay with formula:

$$G = \frac{A_{600T} - A_{600B}}{A_{600N} - A_{600B}}$$

$$Ir = \frac{A_{420T} - A_{420B}}{A_{420N} - A_{420B}} \times \frac{1}{G}$$

G—growth factor, which indicates the survival of the microorganis and its ability to maintain activity after treatment with toxic substance;

Ir—induction rate, which indicates induced expression of mumC after treatment with toxic substance;

$A_{600}$—absorbance of the sample at 600 nm;
$A_{600B}$—absorbance of blank control at 600 nm;
$A_{600N}$—absorbance of negative control at 600 nm;
$A_{420T}$—absorbance of the sample at 420 nm;
$A_{420B}$—absorbance of blank control at 420 nm;
$A_{420N}$—absorbance of negative control at 420 nm;

TABLE 1

Injury degree comparison after treatment with plasma jet under different temperature

| Temperature of plasma jet/° C. | G | Ir |
|---|---|---|
| 28 | 0.5711 | 2.8524 |
| 34 | 0.4674 | 3.6293 |
| 37 | 0.4760 | 3.8419 |
| 40 | 0.4412 | 3.3118 |
| 45 | 0.5543 | 2.7761 |

Conclusion: from table 1 it can be seen that from 28° C., G value keeps decreasing and Ir value keeps increasing with the increase of the plasma jet temperature, indicating that increase of the temperature causes lethal effect on S. typhimurium NM2009 or inhibit its growth and also enhanced DNA injury degree and result in emergency repair system of microbes. When the plasma temperature is higher than 40° C., there is fluctuation in G value and Ir decreases significantly, indicating that part of the bacteria appears to be resistant to the growth and the injury degree decreases. From table 1 it can be seen that, when the plasma jet temperature is 34~40° C., plasma jet which can induce relatively high DNA injury degree can be maintained so that to induce emergency repair system in microorganism and result in effective mutation.

Example 2

Mortality Rate Induced by Plasma Jet at 37±3° C. for Mutation

1. Bacteria strain: E. coli ACCC01626.
2. Culture medium and equipment

LB liquid culture medium: tryptone 1%, yeast extract 0.5%, sodium chloride 1%, distilled water.

LB solid culture medium: tryptone 1%, yeast extract 0.5%, sodium chloride 1%, agar 2%, distilled water.

Other: 0.8% physiological saline, 10% glycerol, pipette tip, spreader, centrifuge tube and EP tube.

Sterilization condition: 121° C. for 20 min

3. Experimental Procedure (1) Inoculate E. coli to LB liquid culture medium (50 mL/250 mL), and culture at 37° C., 200 rpm for 12 h.

(2) Take certain amount of the bacteria solution (around 3 mL), centrifuge at 4000 rmp for 5 min, wash the bacteria by physiological saline twice, and resuspend in certain amount of physiological saline to a final concentration of $10^6$-$10^8$ cells/mL ($A_{600}$ between 0.6 and 0.8).

(3) Because bacteria is sensitive to dry, glycerol at a final concentration of 5% is added to the bacteria solution (1:1 mix the bacteria solution and 10% glycerol).

(4) Take 10 μl bacteria suspension onto a slide, and spread evenly, set the mutagenesis parameter as: power 120 w, gas flow 10 SLM, 2 mm distance between nozzle 12 of plasma generator and the sample, 30 s treatment time. Start mutagenesis by using the device of the invention on 8 samples continuously. During the treatment, the treated sample will be replaced by the next one to be treated automatically within 5 s time interval. During the mutation, the temperature sensor detected the temperature of the plasma jet, and it is shown that the plasma jet temperature was kept stably at 37±3□ during the whole process on the 8 samples.

(5) The slide was put into EP tube (containing 1 mL physiological saline) after mutagenesis.

(6) Shake the EP tube with the slide for 1 min, and take 100 μL to spread onto the LB culture medium plate, culture at 37□ for 16 h.

(7) Count colonies grown on LB culture medium plate and calculate the mortality rate by the following formula:

Mortality rate=(colony number after mutagenesis/ colony number without mutagenesis)×100%

TABLE 2

| | Mortality rate of 8 continuously processed sample | | | | | | | |
|---|---|---|---|---|---|---|---|---|
| No. | 1 | 2 | 3 | 4 | 5 | 6 | 7 | 8 |
| Mutagenesis time (second) | 30 | 30 | 30 | 30 | 30 | 30 | 30 | 30 |
| Mortality rate | 75.3% | 73.4% | 73.6% | 74.6% | 72.2% | 72.9% | 73.5% | 73.8% |

Conclusion: By using the device of the invention, the plasma jet temperature is controlled at the range of 37±3° C., and in the case that other parameters are all the same, the mortality rate of the samples in different batches fluctuates in a small range, indicating that the device of the invention can stably treats multiple samples for a long term.

It should be note that above specific embodiments are for the skilled person in the art to understand the invention more comprehensively, but not to limit the invention in any way. Therefore, although figures and examples of the description have illustrated the invention in detail, it should be understood that modifications and equivalent replacement can be made to the invention. In conclusion, any technical solution and its modification which are not beyond the spirit and scope of the invention are included in the scope the invention.

What is claimed is:

1. A plasma induced mutation breeding device, which comprises:
   a sample treatment system including a sterile working compartment free of bioactive contaminant, a plasma generator, and radio frequency (RF) power module connected with the plasma generator;
   a cooling system for cooling the plasma generator;
   a detection system including a gas flow controller for controlling the gas flow which generates the plasma jet and a temperature sensor for detecting the temperature of the jet emitted by the plasma generator; and
   a control system with an operation panel and a controller for controlling the operation of the mutation breeding device, wherein the controller is connected with the RF power module, gas flow controller, temperature sensor, cooling system as well as the operation panel, respectively, and
   said plasma generator stably emits a plasma jet at 37±3° C. during the biological sample processing,
   wherein the temperature sensor feedback the result of the detected jet temperature to the control system and according to the result, the cooling system maintains the temperature of the plasma jet emitted by the plasma generator at 37±3° C. during the whole sample treatment process,
   and the RF power module includes a RF power and an adaptor which automatically matches the RF power, and said RF power is connected with the plasma generator via the adaptor,
   the adaptor detects the above temperature change of the plasma generator and then feedback the signal to RF power, thereby RF power adjusts the RF it emits according to the feedback signal.

2. The plasma induced mutation breeding device of claim 1, wherein the sample treatment system, detection system and controller are disposed within one housing, the cooling system is disposed outside the housing, the housing is an aluminum profiles housing, and the sterile working compartment has an installation position for a sterilization mean.

3. The plasma induced mutation breeding device of claim 1, wherein the plasma generator has a coaxial structure, and the volume of the sample to be treated is not more than 200 µl.

4. The plasma induced mutation breeding device of claim 1, wherein the plasma generator has a flat structure, and the volume of the sample to be treated is 0.1 mL-10 mL.

5. The plasma induced mutation breeding device of claim 1, wherein a stepped motor and a loading stage are disposed within the sterile working compartment, and the controller lift or horizontally rotate the loading stage by controlling the stepped motor to automatically treat multiple samples and also control the rotation speed of the loading stage to replace the treated sample with the next one to be treated within a 5 second interval.

6. The plasma induced mutation breeding device of claim 1, wherein a carrier conveyor, a sample injector, and a sample recovery belt are disposed within the sterile working compartment.

7. The plasma induced mutation breeding device of claim 6, wherein within 5 seconds after being added by the sample injector, the sample is delivered by the carrier conveyor to a position under the nozzle for jetting, and then the treated sample is recovered by the sample recovery belt within 5 seconds.

8. The plasma induced mutation breeding device of claim 7, wherein a container accommodating protective agent for recovering the sample is disposed on the sample recovery belt.

* * * * *